United States Patent [19]

Okazaki et al.

[11] Patent Number: 5,118,887
[45] Date of Patent: Jun. 2, 1992

[54] PROCESS FOR ISOMERIZATION OF HYDROCHLOROFLUOROCARBONS

[75] Inventors: Susumu Okazaki, Mito; Masatsune Ogura, Ichikawa; Yasunobu Mochizuki, Fuji, all of Japan

[73] Assignee: DuPont-Mitsui Fluorochemicals Co., Ltd., Tokyo, Japan

[21] Appl. No.: 676,279

[22] Filed: Mar. 28, 1991

[30] Foreign Application Priority Data

Mar. 31, 1990 [JP] Japan ................................. 2-83000

[51] Int. Cl.$^5$ .............................................. C07C 17/24
[52] U.S. Cl. ..................................... 570/151; 570/134
[58] Field of Search ............................... 570/151, 134

[56] References Cited

U.S. PATENT DOCUMENTS

| | | | |
|---|---|---|---|
| 4,508,849 | 4/1985 | Inoue et al. | 502/263 |
| 4,902,838 | 2/1990 | Manzer et al. | 570/151 |

FOREIGN PATENT DOCUMENTS 121710  3/1977  Japan ................................. 570/151

OTHER PUBLICATIONS

Presentation made on Oct. 5, 1989 at the 20th Annual Meeting of Union of Chemistry-Related Societies in the Chubu Area, Japan, at the Shizouka University (In English).

Primary Examiner—Howard T. Mars
Assistant Examiner—Kimberly J. Kestler
Attorney, Agent, or Firm—Webb, Burden, Ziesenheim & Webb

[57] ABSTRACT

A partially fluorinated alumina catalyst having a determined component, which is obtained by calcining an $Al_2O_3 \cdot nH_2O$ (n=0 to 3) containing fibril of polytetrafluoroethylene, provides an excellent catalyst for the isomerization of HCFCs.

11 Claims, No Drawings

PROCESS FOR ISOMERIZATION OF HYDROCHLOROFLUOROCARBONS

BACKGROUND OF THE INVENTION

This invention relates to a process for isomerization of hydrochlorofluorocarbons, particularly to a process for isomerization of hydrochlorofluorocarbons to more stable isomers using fluorinated alumina catalyst.

Among the chlorofluoroalkanes (which are commonly named "flon"), perchlorofluorocarbons (containing only fluorine and chlorine, and no hydrogen) (hereinafter abbreviated as "CFC") have been widely used as refrigerant carriers, solvents, foaming agents and so on, as they are stable and safe substances.

But recently, as CFCs were found to be one of the substances to be the cause of the destruction of the ozone layer and global warming, an international agreement was concluded to restrict the production of CFCs by 2,000 A.D. completely.

Recently, research and study of substances for the substitution of these CFCs has been conducted. As the most possible substitution, hydrogen-containing chlorofluoroalkanes, namely hydrochlorofluorocarbons (hereinafter abbreviated as "HCFCs"), such as: 1,1-dichloro-2,2,2-trifluoroethane (hereinafter abbreviated as "HCFC-123"); 1-chloro-1,2,2,2-tetrafluoroethane (hereinafter abbreviated as "HCFC-124"); and 2-chloro-2,2-difluoroethane (hereinafter abbreviated as "HCFC-142b"), can be listed.

However, HCFCs have many kinds of isomers. For example, dichlorotrifluoroethane has isomers of 1,2-dichloro-1,2,2-trifluoroethane (hereinafter abbreviated as "HCFC-123a"), 2,2-dichloro-1,1,2-trifluoroethane (hereinafter abbreviated as "HCFC-123b") and the like, besides the above-mentioned HCFC-123.

In the synthesis of HCFC-123, the by-products of these isomers may sometimes be produced. Similarly, in the synthesis of HCFC-142b, 2-chloro-1,2-difluoroethane (hereinafter abbreviated as "HCFC-142a") and 1-chloro 2,2-difluoroethane (hereinafter abbreviated as "HCFC-142") may be sometimes produced as by-products.

HCFCs such as HCFC-123a, HCFC-123b and 1-chloro-1,1,2,2-tetrafluoroethane (hereinafter abbreviated as "HCFC-124a") are more unstable compounds than the HCFCs which have a high concentration of fluorine atoms around a carbon atom in the molecule such as HCFC-123 and HCFC-124, particularly those HCFCs having trifluoromethyl radicals ($CF_3$). Stable compounds are generally preferred for most applications. For example, as in the case of use as the foaming agent of urethane foam, mixing such highly reactive HCFCs with other materials threatens to influence the quality of the product, so it is not preferable. For such application, the use of HCFCs which have a high concentration of fluorine atoms around a carbon atom, is desirable. For example, in an HCFC having more than 3 fluorine atoms in the molecule, an HCFC having the trifluoromethyl radical in the molecule (such as HCFC-123 and HCFC-124) is the most preferable. And also by way of example in dichlorodifluoroethane and chlorodifluoroethane having only 2 fluorine atoms in the molecule, 1,2-dichloro-2,2-difluoroethane (hereinafter abbreviated as "HCFC-132b") and HCFC-142b which have the difluorochloromethyl radical and have a higher concentration of halogen atoms around a carbon atom in the molecule are more preferable.

It would be quite useful if a desired HCFC could be purified and separated from its isomer mixture. However, the boiling point of such isomers are usually so close to each other that purification by the distillation process (which is industrially the most generally used separation means) is not feasible or if feasible is not economical.

DESCRIPTION OF THE PRIOR ART

As the method for the solution of this problem, isomerization of HCFC-123a and the like to HCFC-123 at 100° to 200° C. by using catalysts is known. As the catalysts of such isomerization reaction, for example, alumina catalysts chlorinated and fluorinated by flon, HF and the like have been proposed. However, this method has the defect that the catalytic activity declines quite quickly.

And also, as the method of preventing the decline of the catalytic activity, the method of isomerization by contacting the mixture of a perhalogenated carbon and HCFC-123a with the above-mentioned chlorinated and fluorinated alumina is known (Japanese patent publication (Kokoku) 27375/1986), but this method has the problem of the excessive process necessary to separate HCFC-123 and the perhalogenated carbon after the isomerization reaction. Additionally, the perhalogenated carbon itself that is used as the preventing agent for declining the catalytic activity is the substance causing the destruction of ozone layer.

SUMMARY OF THE INVENTION

As the result of investigating a catalyst of high activity to isomerization and long life in order to solve the above-mentioned problems, inventors of the present invention have found that a partially fluorinated alumina catalyst having a determined component which is obtained by calcining $Al_2O_3 \cdot n\, H_2O$ (n=0 to 3) containing fibril of polytetrafluoroethylene is an excellent catalyst for the isomerization of HCFCs.

That is to say, this invention relates to the process for isomerization of hydrochlorofluorocarbons which comprises contacting hydrochlorofluorocarbons of 2 or 3 carbon atoms with fluorinated alumina catalysts described as the formula $AlF_xO_y$ (where $0 < x/y \leq \frac{2}{3}$). The catalyst is obtained by calcining $Al_2O_3 \cdot n\, H_2O$ (n=0 to 3) containing fibrils of polytetrafluoroethylene at a temperature of at least 400° C.

DESCRIPTION OF THE PREFERRED EMBODIMENT

HCFCs used in the isomerization process of this invention are hydrochlorofluorocarbons of 2 to 3 carbon atoms, particularly hydrochlorofluoroethanes containing hydrogen, chlorine and fluorine.

The isomerization reaction to form the isomer with the higher concentration of the halogen atoms around a carbon atom, particularly with higher concentration of fluorine atoms proceeds by utilizing these HCFCs in a gaseous state, preferably at the temperature of 30 to 300° C., and contacting the gaseous HCFCs with the above-mentioned catalyst.

Some isomers have different electronegativity in the molecule. HCFCs having a trifluoromethyl radical or difluorochloromethyl radical, can be shown as the specific examples of such isomers.

The following are given as examples of the typical isomerization process:

(1) Isomerization of ,1,2-dichloro-1,2,2-trifluoroethane (HCFC-123a) and 2,2-dichloro-1,1,2 trifluoroethane (HCFC-123b) to 1,1-dichloro-2,2,2-trifluoroethane (HCFC-123);

(2) Isomerization of 1-chloro-1,1,2,2-tetrafluoroethane (HCFC-124a) to 1-chloro-1,2,2,2-tetrafluoroethane (HCFC124)[.];

(3) Isomerization of 1,2-dichloro-1,2-difluoroethane (HCFC-132) and 1,1-dichloro-2,2-difluoroethane (HCFC-132a) to 1,2-dichloro-2,2-difluoroethane (HCFC-132b); and (4) Isomerization of 2-chloro-1,2-difluoroethane (HCFC-142a) and 1-chloro-2,2-difluoroethane (HCFC-142) to 2-chloro-2,2-difluoroethane (HCFC-142b); and the like can be listed.

$Al_2O_3 \cdot n\, H_2O$ (n=0 to 3) which is the starting material of manufacturing the catalyst is preferred to be of high purity. $Al_2O_3 \cdot n\, H_2O$ (n=0 to 3) can be prepared by various methods although the catalytic activity of the catalyst depends on the preparation method. For example, the alumina prepared from aluminium alkoxide or aluminium nitrate is of high purity. It gives both high catalytic activity and long catalytic life because organic radicals or acid radicals are decomposed and removed by calcining at temperatures greater than 400° C.

On the other hand, alumina containing nonvolatile acid radicals such as aluminium sulfate and the like shows low catalytic activity and short catalytic life, and alumina containing basic radicals prepared from sodium aluminate and the like also exhibited low catalytic activity.

The preparation of the catalyst of this invention is characterized in that it is calcined, and in that fibrils of polytetrafluoroethylene are contained in the $Al_2O_3 \cdot n\, H_2O$ (n=0 to 3) catalytic starting material. The fibrils of polytetrafluoroethylene which are dispersed homogeneously in the alumina and which are decomposed and removed by calcining not only act as fluorinating agents but also contribute to production of a partially fluorinated catalyst of determined fluoride/oxygen composition having many small holes derived from its fibril structure.

The fibrils of polytetrafluoroethylene mean polytetrafluoroethylene having fine fibrous structure. Polytetrafluoroethylene is a polymer which is easily fibrillated. Particularly, emulsion polymerized polytetrafluoroethylene is easily fibrillated and known to be fibrillated to ultra fine cobwebby filaments, when compression-shear action is added by agitation and the like at moderate temperature (Japanese Patent publication (Kokai) 209645/1984).

The preparation process of the fluorinated alumina catalyst is not restricted particularly, but the most general process is that aluminium compounds containing such easily decomposable and removable radicals by calcining as aluminium alkoxide, aluminium nitrate and the like are dissolved in water, then hydrolized, for example, by aqueous ammonia water to precipitate ammonium hydroxide.

From the precipitate, partially fluorinated alumina catalyst can be obtained by the following methods: (1) polytetrafluoroethylene of easily fibrillable property is added to the precipitate. Heat compression and shear are added to disperse the fibrils of polytetrafluoroethylene in the precipitate homogeneously which is then calcined; (2) After the precipitate is dried and pulverized to powder, polytetrafluoroethylene of easily fibrillable property is added, and compression-shear strength is added to disperse the fibrils of polytetrafluoroethylene in the powder homogeneously which is then calcined; (3) The precipitate is dried, further calcined to get alumina. The alumina is pulverized to powder, and polytetrafluoroethylene of easily fibrillable property is added and compression-shear strength is added to disperse homogeneously the fibrils of polytetrafluoroethylene in the powder which is then calcined.

Any process similar to the above is envisioned within the scope of the present invention.

In the industrial setting, process (3) which can utilize commercial alumina is most useful for the preparation of the catalysts.

Addition of polytetrafluoroethylene of easily fibrillable property is preferably more than 0.3 wt% per alumina to $Al_2O_3 \cdot n\, H_2O$ (n=0 to 3). The upper limit is not restricted but about less than 15 wt% is preferable. The reason is that above 15 wt% results in a higher preparation cost of the catalyst and tends to reduce in some degree the catalytic activity. Less than 0.3 wt% is not preferable as the catalytic activity is reduced.

The lower limit of the calcining temperature of the catalyst is necessarily more than 400° C. which is the decomposition temperature of polytetrafluoroethylene. The upper limit is not necessarily restricted, but the higher the temperature, the more the catalytic activity tends to be lowered. A temperature of less than ,1000° C. is desired, particularly 600° C. to 900° C. is preferred.

The thus obtained catalyst is a partially fluorinated alumina catalyst described by the general formula $AlF_xO_y$ (in the formula, $0 < x/y \leq \frac{2}{3}$). Namely, it is necessary that at least part of the catalyst of this invention is fluorinated. With alumina catalysts having no fluorine, the isomerization activity is low. On the other hand, if fluorination proceeds to $x/y > \frac{2}{3}$, the activity also becomes lower.

Fluorine content by x-ray photoelectron spectrum analysis ("xps") is within the range of about 1 to 33 mol%, preferably the range of fluorine content in the catalyst with high catalytic activity is about 2 to 10%.

As for the reaction condition of the isomerization of HCFC of this invention, the temperature may suitably be higher than the boiling point of HCFC of the reactant and lower than the decomposition temperature (about 300° C.). Comparing with the optimum reaction temperature range (about 100° to 150° C.) of the hitherto known partially fluorinated alumina catalyst treated by flons, the catalytic activity used in the invention is higher and then the optimum reaction temperature condition can be obtained between 30° to 100° C., which is more than 50° C. lower than hitherto known alumina catalysts. As a result, the catalytic life can be lengthened more than 3 times.

EXAMPLES

EXAMPLE 1

To 1.7 kg of the pure water heated at 100° C., 70g of aluminium isopropoxide was added agitatingly and hydrolyzed for 3 hours. After leaving to stand for one day, it was rinsed and filtered to get filter cake (aluminium hydroxide). Then, the filter cake was converted into mortar. 0.875g of polytetrafluoroethylene of easy fibrillability ("Teflon" K10-J made at DuPont-Mitsui Fluorochemicals Co., Ltd.) was added and mixed for about 3 minutes and dried for one hour at about 100° C. Then, polytetrafluoroethylene of easy fibrillability was kneaded to be untwisted, keeping whole filter cake in the wet and warm condition, and was fibrillated, after that, kneading and drying was repeated 3 to 4 times for 60 minutes.

The filter cake containing thus obtained polytetrafluoroethylene fibrils was dried for day at 120° C., and pulverized to the powder of uniform 22 to 40 mesh. 1.2 g of the powder was put into reactor tube and calcined for 3 hours at 600° C. in $N_2$ stream to get fluorinated alumina catalyst.

The elemental analysis values of aluminium, fluorine and oxygen in the catalyst by xps analysis are shown in Table 1.

Then, by using HCFC-123 containing 10% of HCFC-123a as the raw material of the isomerization, HCFC-123a was isomerized to HCFC-123 at 120 ml/min(gas) of the feeding rate of the raw material and 60° C. of the reaction temperature by the above-mentioned catalyst. The conversion rate of the isomerization of HCFC-123a to HCFC-123 after 1 hour and 3 hours is shown in Table 2.

EXAMPLE 2

The isomerization reaction was carried out in the same condition as Example 1 except varying the reaction temperature at 40° C. by using the catalyst of the example 1.

The results are shown in Table 2.

EXAMPLE 3

0.35 g of polytetrafluoroethylene of easy fibrillability was added under the same conditions as in Example 1, fluorinated alumina catalyst was prepared. The elemental analysis values of the catalyst are shown in Table 1.

By using this catalyst, except for varying the reaction temperature to 80° C., the isomerization reaction was carried out in the same condition as in Example 1. The results are shown together in table 2.

EXAMPLE 4

Alumina catalyst (N611N made at Nikki Kagaku Co) was pulverized, 0.35g of polytetrafluoroethylene of easily fibrillable property was added and mixed for nearly 3 minutes and heated for 30 minutes at about 80° C. In the warm condition, polytetrafluoroethylene of easily fibrillable property was kneaded to be untwisted and fibrillated. 1.2g of the mixture was put into a reactor tube and calcined for 3 hours at 600° C. in $N_2$ stream to obtain fluorinated alumina catalyst. The elemental analysis values of the catalyst are shown in Table 1.

By using HCFC-123 containing 10% of HCFC-123a as the raw material of the isomerization reaction, HCFC-123a was isomerized to HCFC-123 at 120ml/min(gas) of the feed rate of the raw material at 80° C. of the reaction temperature by the use of this catalyst.

The result is shown in table 2.

Comparative example 1

Into 1.7kg of pure water heated at 100° C., 70g of aluminium isopropoxide was added. The mixture was agitated and hydrolyzed for 3 hours. After leaving to stand for one day, it was rinsed and filtered to obtain filter cake (aluminium hydroxide). Then, it was dried for 1 day at 120° C. and pulverized to powders of uniform 22 to 40 mesh. 1.2g of the powders were put into a reactor tube and calcined for 3 hours at 600° C. in $N_2$ stream to obtain alumina catalyst.

As the raw material of the isomerization reaction, HCFC-123 containing 10% of HCFC-123a was used. By the use of this catalyst, HCFC-123a was isomerized to HCFC-123 at 120 ml/min(gas) of the feed rate of the raw materials at 60° C. of the reaction temperature.

The result is shown in table 2.

Comparative example 2

Alumina catalyst (Made at Nikki Kagaku Co. N611N) was pulverized to powders of uniform 22 to 40 mesh. 1.2g of the powders was put into a reactor tube and calcined for 3 hours at 600° C. in $N_2$ stream to obtain catalyst.

By using HCFC-123 containing 10% of HCFC-123a as the raw material of the isomerization reaction, by this catalyst, HCFC-123a was isomerized to HCFC-b 123 at 120 ml/min(gas) of the feed rate of the raw materials at 60° C. of the reaction temperature.

The result is shown in Table 2.

Comparative example 3

Alumina catalyst (Made at Nikki Kagaku Co. N611N) was pulverized to powders of uniform 22 to 40 mesh. 1.2g of the powders was put into a reactor tube, calcined for 3 hours at 600° C. in $N_2$ stream and then introduced with the mixing gas of $CFC-13/N_2$ (12/88 vol%) at the rate of 150 ml/min to obtain partially fluorinated alumina catalysts activated for 10 min at 420° C. The elemental analysis values of the catalyst by xps analysis are shown in table 1. Comparing with the catalyst of examples 1, 2 and examples 3, 4, the degree of the fluorination is more advanced. It is the catalyst containing a small amount of chlorine.

By using HCFC-123 containing 10% of HCFC-123a as the raw material of the isomerization reaction by this catalyst, HCFC-123a was isomerized to HCFC-123 at the feed rate of the raw materials of 120 ml/min(gas) at the reaction temperature of 120° C.

The result is shown in table 2.

Comparative example 4

An alumina catalyst containing alkali metal, N611A made at Nikki Kagaku Co was used. In the same method as in comparative example 3, calcination and activation were carried out to obtain partially fluorinated catalysts.

By using HCFC-123 containing 10% of HCFC-123a as the raw material of isomerization reaction, HCFC-123a was isomerized to HCFC-123 at the feed rate of the raw materials of 120 ml/min(gas) at the reaction temperature of 120° C.

TABLE 1

| | Element analysis values of the catalyst. | | |
| | Element analysis values | | |
| | Example 1, 2 | Example 3, 4 | Comparative Example 3 |
|---|---|---|---|
| Al | 35.5%(1) | 37.3%(1) | 32.4%(1) |
| F | 8.3%(0.2) | 3.9%(0.1) | 23.2%(0.7) |
| O | 56.2%(1.6) | 58.8%(1.6) | 44.2%(1.4) |
| Cl | | | 0.2%(0.1) |

Note:
() show the element ratio of the content.

TABLE 2

The conversion rate of the isomerization of HCFC-123a to HCFC-123.

| | Conversion rate of isomerization reaction % | |
|---|---|---|
| | After 1 hour | After 3 hours |
| Example 1 | 99.9 | 85.0 |
| Example 2 | 95.0 | 88.0 |
| Example 3 | 99.5 | 80.0 |
| Example 4 | 98.0 | 65.0 |
| Comparative Example 1 | 3.5 | 0.0 |
| Comparative Example 2 | 35.5 | 4.0 |
| Comparative Example 3 | 85.0 | 0.0 |
| Comparative Example 4 | 0.3 | 0.0 |

As clarified from the result of table 2, in the isomerization reaction by using the catalyst of this invention, conversion rate of the isomerization of HCFC-123a to HCFC-123 is higher and furthermore the declining of the catalytic activity after aging is smaller. On the contrary, in the comparative example 1 and comparative example 2 using alumina catalyst, the activity is extraordinarily low. In the case of using alumina catalyst chloro-fluorinated by flon, depending on alumina used as a raw material, a rather high level of initial activity can be obtained but activity declines rapidly with the passage of time.

EFFECT OF THE INVENTION

According to the present invention, using partially fluorinated alumina catalyst obtained by calcining $Al_2O_3 \cdot nH_2O$ (n=0 to 3) containing fibrils of polytetrafluoroethylene as catalyst, HCFCs can be isomerized at high conversion rate, furthermore the catalyst life is longer and HCFC of high utilization values can be obtained as the substitution for CFC, so that the contribution to solve the global environment problems caused by flon is exceedingly great.

Hydrochlorofluorocarbon (HCFC) of 2 or 3 carbon atoms can be used as a substitute for perchlorofluorocarbons to achieve less destruction to the Earth's ozone layer. However, many kinds of isomers exist in these HCFCs. Among them, HCFCs having a lower concentration of halogen atoms around a carbon atom in the molecule is unstable so that this invention relates to the isomerization process of converting HCFC isomers of low halogen concentration to HCFCs of high halogen concentration of atoms in the molecule.

The isomerization of this invention is carried out by using a fluorinated alumina catalyst described in the formula $AlF_xO_y$ (in the formula, $0 < x/y \leq \frac{2}{3}$), which is obtained by calcining $Al_2O_3 \cdot nH_2O$ (n=0 to 3) containing fibrils of polytetrafluoroethylene as catalyst at a temperature of at least 400° C.

We claim:

1. A process for the isomerization of hydrochloroflurocarbon, which comprises contacting:
   a) a mixture of one or more isomers of one or more hydrochlorofluorocarbon compounds in a gaseous state, said hydrochlorofluorocarbons having 2 to 3 carbon atoms; with
   b) a fluorinated alumina catalyst described by the formula $AlF_xO_y$, (in the formula, $0 < x/y \leq \frac{2}{3}$);
   wherein said catalyst is obtained by calcining $Al_2O_3 \cdot nH_2O$ (n=0 to 3) containing fibrils of polytetrafluoroethylene at a temperature of at least 400° C.

2. The isomerization process according to claim 1 wherein hydrochlorofluorocarbon is hydrochlorofluoroethane.

3. The isomerization process according to claim 2 which comprises isomerizing 1,2-dichloro-1,2,2-trifluoroethane (HCFC-123a) and 2,2-dichloro-1,1,2-trifluoroethane (HCFC-123b) to 1,1-dichloro-2,2,2-trifluoroethane (HCFC-123).

4. The isomerization process according to claim 2 which comprises isomerizig 1-chloro-1,1,2,2-tetrafluoroethane (HCFC-124a) to 1-chloro-1,2,2,2-tetrafluoroethane (HCFC-124).

5. The isomerization process according to claim 2 which comprises isomerizing 1,2-dichloro-1,2 difluoroethane (HCFC-132) and 1,1-dichloro-2,2-difluoroethane (HCFC-132a) to 1,2-dichloro-2,2-difluoroethane (HCFC-132b).

6. The isomerization process according to claim 2 which comprises isomerizing 2-chloro-1,2 difluoroethane (HCFC-142a) and 1-chloro-2,2 difluoroethane (HCFC-142) to 2 chloro-2,2-difluoroethane (HCFC-142b).

7. The isomerization process according to claim 1 characterized in that said catalyst of said formula $Al_2O_3 \cdot nH_2O$ (n=0 to 3) containing fibrils of polytetrafluoroethylene is calcined at the temperature of 400° C. to 1000° C.

8. The isomerization process according to claim 1 characterized in that said catalyst of said formula $Al_2O_3 \cdot nH_2O$ (n=0 to 3) containing fibrils of polytetrafluoroethylene is calcined at the temperature of 600° C. to 900° C.

9. The isomerization process according to claim 1 characterized in that said isomerization process is carried out at a temperature between the boiling point of said hydrochlorofluorocarbons and the decomposition temperature of said hydrochlorofluorocarbons.

10. The isomerization process according to claim 9 wherein said temperature is between 30° C. to 300° C.

11. The isomerization process according to claim 9 wherein said temperature is between 30° C. to 100° C.

* * * * *

UNITED STATES PATENT AND TRADEMARK OFFICE
CERTIFICATE OF CORRECTION

PATENT NO. : 5,118,887

DATED : June 2, 1992

INVENTOR(S) : Susumu Okazaki, Masatsune Ogura and Yasunobu Mochizuki

It is certified that error appears in the above-identified patent and that said Letters Patent is hereby corrected as shown below:

Abstract Line 5 after "HCFCs" insert --from HCFCs of low halogen concentration within the molecule to HCFCs of high halogen concentration in the molecule--.

Column 2 Line 48 "calcining n" should read --calcining--.

Column 3 Line 3 after "of" delete ",".

Column 3 Line 9 "(HCFC124)[.]" should read --(HCFC-124)--.

Column 3 Line 13 begin new paragraph with "(4)".

Column 3 Line 28 "nonvolatile" should read --non-volatile--.

Column 3 Line 65 after "shear" insert --strength--.

Column 4 Lines 11-12 delete "Any process similar to the above is envisioned within the scope of the present invention.".

UNITED STATES PATENT AND TRADEMARK OFFICE
CERTIFICATE OF CORRECTION

PATENT NO. : 5,118,887

DATED : June 2, 1992

INVENTOR(S) : Susumu Okazaki, Masatsune Ogura and Yasunobu Mochizuki

It is certified that error appears in the above-identified patent and that said Letters Patent is hereby corrected as shown below:

Column 4 Line 29 after "than" delete --,--.

Column 5 Line 7 after "for" insert --1--.

Column 5 Line 43 "Co)" should read --Co.)--.

Column 6 Line 48 "Co" should read --Co.--.

Column 6 Line 56 after "120° C." add new paragraph, --The results are shown in table 2.--.

Claim 1 Line 8 Column 8 "to" should read --or--.

Claim 8 Line 45 Column 8 "to." should read --to--.

Signed and Sealed this

Second Day of November, 1993

Attest:

BRUCE LEHMAN

Attesting Officer

Commissioner of Patents and Trademarks